(12) United States Patent
Dai

(10) Patent No.: US 7,087,733 B2
(45) Date of Patent: Aug. 8, 2006

(54) HUMAN ARL-RELATED GENE VARIANTS ASSOCIATED WITH CANCERS

(76) Inventor: Ken-Shwo Dai, 1F., No. 18, Industry E. Rd., IV, Science-Based Industrial Park, Hsinchu (TW)

( * ) Notice: Subject to any disclaimer, the term of this patent is extended or adjusted under 35 U.S.C. 154(b) by 74 days.

(21) Appl. No.: 10/653,681

(22) Filed: Sep. 2, 2003

(65) Prior Publication Data

US 2005/0048503 A1 Mar. 3, 2005

(51) Int. Cl.
*C07H 21/02* (2006.01)
*C07H 21/04* (2006.01)

(52) U.S. Cl. .................. 536/23.1; 536/23.1
(58) Field of Classification Search .............. 536/23.1
See application file for complete search history.

(56) References Cited

U.S. PATENT DOCUMENTS 6,630,574 B1 * 10/2003 Wang et al. ............ 530/350

OTHER PUBLICATIONS

GenBank database for expressed sequence tags, National Center for Biotechnology information, National Library of Medicine, NIH (Bethesda, MD, USA) Accession No. BM 793014 (Mar. 5, 2002).*
Andrew Chin, "On the preperation and utilization of isolated and purified oligonucleotides" [electronic resource], UNC Library, Mar. 14, 2002.*
Deliang Cao, et al.; Identification and Characterization of a Novel Human Aldose Reductase-Like Gene, vol. 273, No. 19, Issue of May 8, pp. 11429-11435 1998.
"On the preparation and utilization of isolated and purified oligonucleotides" [electronic resource], Andrew Chin, allegedly deposited in UNC library on Mar. 14, 2002, date of publication, if any, is in question.
Cao et al., J. biol. Chem., 273: 11429-35 (1998).
Cao et al., Nucleotide Accession No. U37100.
Han, Z. EST Accession No. AV683595.
Han, Z. EST Accession No. AV698712.
Han, Z. EST Accession No. AV691243.
Strausberg, R. EST Accession No. BQ221381.

* cited by examiner

*Primary Examiner*—Jeff Siew
*Assistant Examiner*—Brandon Fetterolf
(74) *Attorney, Agent, or Firm*—Ladas and Parry LLP

(57) ABSTRACT

The invention relates to the nucleic acid sequences of two novel human ARL-related gene variants (ARLV1 and ARLV2) and the polypeptides encoded by ARLV1 and ARLV2.

The invention also relates to the process for producing the polypeptides encoded by ARLV1 and ARLV2.

The invention further relates to the use of the nucleic acid of ARLV1 and ARLV2 and the polypeptide encoded by ARLV1 and ARLV2 in diagnosing diseases associated with the deficiency of human ARLV gene, in particular large cell lung cancer or hepatocellular carcinoma.

5 Claims, 16 Drawing Sheets

FIG.1A

```
CAAAAACAGCAACAGAAAGCAGGACGTGAGACTTCTACCTGCTCACTCAGAATCATTTCT    60

GCACCAACCATGGCCACGTTTGTGGAGCTCAGTACCAAAGCCAAGATGCCCATTGTGGGC   120
          M   A   T   F   V   E   L   S   T   K   A   K   M   P   I   V   G    17

CTGGGCACTTGGAAGTCTCCTCTCGGCAAAGTGAAAGAAGCAGTGAAGGTGGCCATTGAT   180
  L   G   T   W   K   S   P   L   G   K   V   K   E   A   V   K   V   A   I   D    37

GCAGGATATCGGCACATTGACTGTGCCTATGTCTATCAGAATGAACATGAAGTGGGGGAA   240
  A   G   Y   R   H   I   D   C   A   Y   V   Y   Q   N   E   H   E   V   G   E    57

GCCATCCAAGAGAAGATCCAAGAGAAGGCTGTGAAGCGGGAGGACCTGTTCATCGTCAGC   300
  A   I   Q   E   K   I   Q   E   K   A   V   K   R   E   D   L   F   I   V   S    77

AAGTTGTGGCCCACTTCCAGATCGAGAAGCTCTTGAACAAACCTGGACTGAAATATAAAC   360
  K   L   W   P   T   S   R   S   R   S   S   *                                   88
```

FIG.1B

```
CAGTGACTAACCAGGTTGAGTGTCACCCATACCTCACGCAGGAGAAACTGATCCAGTACT  420

GCCACTCCAAGGGCATCACCGTTACGGCCTACAGCCCCTGGCTCTCCGGATAGACCTT    480

GGGCCAAGCCCAGAAGACCCCTTCCCTGCTGGAGGATCCCAAGATTAAGGAGAGATTGCTGCAA  540

AGCACAAAAAAACCGCAGCCCAGGTTCTGATCCGTTTCCATATCCAGAGGAATGTGATTG  600

TCATCCCCCAAGTCTCTGTTGACACCAGCACGCCATTGTTGAGAACATTCAGGTCTTTGACTTTA  660

AATTGAGTGATGAGGAGATGGCAACCATACTCAGCTTCAACAGAAACTGGAGGGCCTGTA  720

ACGTGTTGCAATCCCTCTCATTTGGAAGACTATCCCTTCGATGCAGAATATTGAGGTTGAA  780
```

FIG.1C

TCTCCTGGTGAGATTATACAGGAGATTCTCTCTTTCTTCGCTGAAGTGTGACTACCTCCACT 840

CATGTCCCATTTTAGCCAAGCTTATTTAAGATCACAGTGAACTTAGTCCTGTTATAGACG 900

AGAATCGAGGTGCTGTTTTAGACATTTATTTCTGTATGTTCAACTAGAGGATCAGAATATCA 960

CAGAAAAGCATGGCTTGAATAAGGAAATGACAATTTTTCCACTTATCTGATCAGAACAA 1020

ATGTTTATTAAGCATCAGAAACTCTGCCAACACTGAGGATGTAAAGATCAATAAAAAAAA 1080

TAATAATCAT 1090

FIG.2A

```
CAAAAACAGCAACAGAAAAGCAGGACGTGAGACTTCTACCTGCTCACTCAGAATCATTTCT    60

GCACCAACCATGGCCACGTTTGTGGAGCTCAGTACCAAAGCCAAGATGCCCATTGTGGGC   120
          M   A   T   F   V   E   L   S   T   K   A   K   M   P   I   V   G    17

CTGGGCACTTGGAAGTCTCCTCTCGGCAAAGTGAAAGAAGCAGTGAAGGTGGCCATTGAT   180
 L   G   T   W   K   S   P   L   G   K   V   K   E   A   V   K   V   A   I   D    37

GCAGGATATCGGCACATTGACTGTGCCTATGTCTATCAGAATGAACATGAAGTGGGGGAA   240
 A   G   Y   R   H   I   D   C   A   Y   V   Y   Q   N   E   H   E   V   G   E    57

GCCATCCAAGAGAAGATCCAAGAAAAGCTGTGAAGCGGAGGACCTGTTCATCGTCAGC   300
 A   I   Q   E   K   I   Q   E   K   A   V   K   R   E   D   L   F   I   V   S    77

AAGTTGTGGCCCACTTTCTTTGAGAGACCCCTTGTGAGGAAAGCCTTTGAGAAGACCCTC   360
 K   L   W   P   T   F   F   E   R   P   L   V   R   K   A   F   E   K   T   L    97

AAGGACCTGAAGCTGAGCTATCTGGACGTCTATCTTATTCACTGGCCACAGGGATTCAAG   420
 K   D   L   K   L   S   Y   L   D   V   Y   L   I   H   W   P   Q   G   F   K   117

TCTGGGGATGACCTTTTCCCCAAAGATGATAAAGGTAATGCCATCGGTGGAAAAGCAACG   480
 S   G   D   D   L   F   P   K   D   D   K   G   N   A   I   G   G   K   A   T   137
```

FIG.2B

```
TTCTTGGATGCCTGGGAGGAGGCCATGGAGGAGCTGGTTGATGAGGGGCTGGTGAAAGCCCTT     540
 F   L   D   A   W   E   A   M   E   E   L   V   D   E   G   L   V   K   A   L      157
GGGGTCTCCAATTTCAGCCACTTCCAGATCGAGAAGCTCTTGAACAAACCTGGACTGAAA        600
 G   V   S   N   F   S   H   F   Q   I   E   K   L   L   N   K   P   G   L   K      177
TATAAACCAGTGACTAACCAGGTTGAGTGTCACCCATACCTCACGCAGGAGAAACTGATC        660
 Y   K   P   V   T   N   Q   V   E   C   H   P   Y   L   T   Q   E   K   L   I      197
CAGTACTGCCACTCCAAGGGCATCACCGTTACGGCCTACAGCCCCCTGGGCTCTCCGGAT        720
 Q   Y   C   H   S   K   G   I   T   V   T   A   Y   S   P   L   G   S   P   D      217
AGACCCTTGGGCCAAGCCAGAAGACCCTTCCCTGCTGGAGGATCCCAAGATTAAGGAGATT       780
 R   P   W   A   K   P   E   D   P   S   L   L   E   D   P   K   I   K   E   I      237
GCTGCAAAGCACTCCCCAAGTCTGTGACACCAGCACGGCATTGTTGAGAACATTCAGGTCT       840
 A   A   K   H   S   P   S   L   *                                                  245
```

FIG.2C

TTGACTTTAAATTGAGTGATGAGGAGATGGCAACCATACTCAGCTTCAACAGAAACTGGA 900

GGGCCTGTAACGTGTTGCAATCCCTCTCATTTGGAAGACTATCCCCTGATGCAGAATATT 960

GAGGTTGAATCTCCCTGGTGAGATTATACAGGAGATTCTCTTTCTTCGCTGAAGTGTGACT 1020

ACCTCCACTCATGTCCCCATTTTAGCCAAGCTTATTTAAGATCACAGTGAACTTAGTCCTG 1080

TTATAGACGAGAATCGAGGTGCTGTTTTAGACATTTATTTCTGTATGTTCAACTAGGATC 1140

AGAATATCACAGAAAAGCATGGCTTGAATAAGGAAATGACAATTTTTCCACTTATCTGA 1200

TCAGAACAAATGTTTATTAAGCATCAGAAACTCTGCCAACACTGAGGATGTAAAGATCAA 1260

TAAAAAAATAATAATCAT 1279

FIG.3A

```
     1                                                                          60
ARLV1  CAAAAACAGCAACAG  AAAGCAGGACGTGAG  ACTTCTACCTGCTCA  CTCAGAATCATTTCT
ARLV2  CAAAAACAGCAACAG  AAAGCAGGACGTGAG  ACTTCTACCTGCTCA  CTCAGAATCATTTCT
ARL    CAAAAACAGCAACAG  AAAGCAGGACGTGAG  ACTTCTACCTGCTCA  CTCAGAATCATTTCT 61                                                                         120
ARLV1  GCACCAACCATGGCC  ACGTTTGTGGAGCTC  AGTACCAAAGCCAAG  ATGCCCATTGTGGGC
ARLV2  GCACCAACCATGGCC  ACGTTTGTGGAGCTC  AGTACCAAAGCCAAG  ATGCCCATTGTGGGC
ARL    GCACCAACCATGGCC  ACGTTTGTGGAGCTC  AGTACCAAAGCCAAG  ATGCCCATTGTGGGC 121                                                                         180
ARLV1  CTGGGCACTTGGAAG  TCTCCTCTCGGCAAA  GTGAAAGAAGCAGTG  AAGGTGGCCATTGAT
ARLV2  CTGGGCACTTGGAAG  TCTCCTCTCGGCAAA  GTGAAAGAAGCAGTG  AAGGTGGCCATTGAT
ARL    CTGGGCACTTGGAAG  TCTCCTCTCGGCAAA  GTGAAAGAAGCAGTG  AAGGTGGCCATTGAT
```

FIG.3B

```
      181
ARLV1 GCAGGATATCGGCAC ATTGACTGTGCCTAT GTCTATCAGAATGAA CATGAAGTGGGGAA      240
ARLV2 GCAGGATATCGGCAC ATTGACTGTGCCTAT GTCTATCAGAATGAA CATGAAGTGGGGAA
ARL   GCAGGATATCGGCAC ATTGACTGTGCCTAT GTCTATCAGAATGAA CATGAAGTGGGGAA

241
ARLV1 GCCATCCAAGAGAAG ATCCAAGAGAAGGCT GTGAAGCGGGAGGAC CTGTTCATCGTCAGC      300
ARLV2 GCCATCCAAGAGAAG ATCCAAGAGAAGGCT GTGAAGCGGGAGGAC CTGTTCATCGTCAGC
ARL   GCCATCCAAGAGAAG ATCCAAGAGAAGGCT GTGAAGCGGGAGGAC CTGTTCATCGTCAGC

301
ARLV1 AAGTTGTGGCCCACT T-------------- --------------- -------------      360
ARLV2 AAGTTGTGGCCCACT TTCTTTGAGAGACCC CTTGTGAGGAAAGCC TTTGAGAAGACCCTC
ARL   AAGTTGTGGCCCACT TTCTTTGAGAGACCC CTTGTGAGGAAAGCC TTTGAGAAGACCCTC
```

FIG. 3C

```
        361                                                                                            420
ARLV1   ------------ ------------ ------------ ------------ ------------ ------------
ARLV2   AAGGACCTGAAGCTG AGCTATCTGGACGTC TATCTTATTCACTGG CCACAGGGATTCAAG
ARL     AAGGACCTGAAGCTG AGCTATCTGGACGTC TATCTTATTCACTGG CCACAGGGATTCAAG 421                                                                                            480
ARLV1   ------------ ------------ ------------ ------------ ------------ ------------
ARLV2   TCTGGGGATGACCTT TTCCCCAAAGATGAT AAAGGTAATGCCATC GGTGGAAAAGCAACG
ARL     TCTGGGGATGACCTT TTCCCCAAAGATGAT AAAGGTAATGCCATC GGTGGAAAAGCAACG 481                                                                                            540
ARLV1   ------------ ------------ ------------ ------------ ------------ ------------
ARLV2   TTCTTGGATGCCTGG GAGGCCATGGAGGAG CTGGTGGATGAGGGG CTGGTGAAAGCCCTT
ARL     TTCTTGGATGCCTGG GAGGCCATGGAGGAG CTGGTGGATGAGGGG CTGGTGAAAGCCCTT
```

FIG.3D

```
       541
ARLV1  ------------ ------------ ---CCAGATC GAGAAGCTCTTGAAC AAACCTGGACTGAAA
ARLV2  GGGGTCTCCAATTTC AGCCACTTCCAGATC GAGAAGCTCTTGAAC AAACCTGGACTGAAA
ARL    GGGGTCTCCAATTTC AGCCACTTCCAGATC GAGAAGCTCTTGAAC AAACCTGGACTGAAA
                                                                      600

601
ARLV1  TATAAACCAGTGACT AACCAGGTTGAGTGT CACCCATACCTCACG CAGGAGAAACTGATC
ARLV2  TATAAACCAGTGACT AACCAGGTTGAGTGT CACCCATACCTCACG CAGGAGAAACTGATC
ARL    TATAAACCAGTGACT AACCAGGTTGAGTGT CACCCATACCTCACG CAGGAGAAACTGATC
                                                                      660

661
ARLV1  CAGTACTGCCCACTCC AAGGGCATCACCGTT ACGGCCTACAGCCCCC CTGGGCTCTCCGGAT
ARLV2  CAGTACTGCCCACTCC AAGGGCATCACCGTT ACGGCCTACAGCCCCC CTGGGCTCTCCGGAT
ARL    CAGTACTGCCCACTCC AAGGGCATCACCGTT ACGGCCTACAGCCCCC CTGGGCTCTCCGGAT
                                                                      720
```

FIG.3E

```
       721
ARLV1  AGACCTTGGGCCAAG  CCAGAAGACCCTTCC  CTGCTGGAGGATCCC  AAGATTAAGGAGATT
ARLV2  AGACCTTGGGCCAAG  CCAGAAGACCCTTCC  CTGCTGGAGGATCCC  AAGATTAAGGAGATT
ARL    AGACCTTGGGCCAAG  CCAGAAGACCCTTCC  CTGCTGGAGGATCCC  AAGATTAAGGAGATT
                                                                      780

781
ARLV1  GCTGCAAAGCACAAA  AAAACCGCAGCCCAG  GTTCTGATCCCGTTTC  CATATCCAGAGGAAT
ARLV2  GCTGCAAAGCAC---  ---------------  ----------------  ---------------
ARL    GCTGCAAAGCACAAA  AAAACCGCAGCCCAG  GTTCTGATCCCGTTTC  CATATCCAGAGGAAT
                                                                      840

841
ARLV1  GTGATTGTCATCCCC  AAGTCTGTGACACCA  GCACGCATTGTTGAG  AACATTCAGGTCTTT
ARLV2  ------TCCCC      AAGTCTGTGACACCA  GCACGCATTGTTGAG  AACATTCAGGTCTTT
ARL    GTGATTGTCATCCCC  AAGTCTGTGACACCA  GCACGCATTGTTGAG  AACATTCAGGTCTTT
                                                                      900
```

FIG.3F

```
     901
ARLV1 GACTTTAAATTGAGT GATGAGGAGATGGCA ACCATACTCAGCTTC AACAGAAACTGGAGG
ARLV2 GACTTTAAATTGAGT GATGAGGAGATGGCA ACCATACTCAGCTTC AACAGAAACTGGAGG
ARL   GACTTTAAATTGAGT GATGAGGAGATGGCA ACCATACTCAGCTTC AACAGAAACTGGAGG
                                                                    960

961
ARLV1 GCCTGTAACGTGTTG CAATCCTCTCATTTG GAAGACTATCCCTTC GATGCAGAATATTGA
ARLV2 GCCTGTAACGTGTTG CAATCCTCTCATTTG GAAGACTATCCCTTC GATGCAGAATATTGA
ARL   GCCTGTAACGTGTTG CAATCCTCTCATTTG GAAGACTATCCCTTC GATGCAGAATATTGA
                                                                   1020

1021
ARLV1 GGTTGAATCTCCCTGG TGAGATTATACAGGA GATTCTCTTTCTTCG CTGAAGTGTGACTAC
ARLV2 GGTTGAATCTCCCTGG TGAGATTATACAGGA GATTCTCTTTCTTCG CTGAAGTGTGACTAC
ARL   GGTTGAATCTCCCTGG TGAGATTATACAGGA GATTCTCTTTCTTCG CTGAAGTGTGACTAC
                                                                   1080
```

FIG.3G

```
      1081                                                                      1140
ARLV1  CTCCACTCATGTCCC  ATTTTAGCCAAGCTT  ATTTAAGATCACAGT  GAACTTAGTCCTGTT
ARLV2  CTCCACTCATGTCCC  ATTTTAGCCAAGCTT  ATTTAAGATCACAGT  GAACTTAGTCCTGTT
ARL    CTCCACTCATGTCCC  ATTTTAGCCAAGCTT  ATTTAAGATCACAGT  GAACTTAGTCCTGTT 1141                                                                      1200
ARLV1  ATAGACGAGAATCGA  GGTGCTGTTTTAGAC  ATTTATTTCTGTATG  TTCAACTAGGATCAG
ARLV2  ATAGACGAGAATCGA  GGTGCTGTTTTAGAC  ATTTATTTCTGTATG  TTCAACTAGGATCAG
ARL    ATAGACGAGAATCGA  GGTGCTGTTTTAGAC  ATTTATTTCTGTATG  TTCAACTAGGATCAG 1201                                                                      1260
ARLV1  AATATCACAGAAAAG  CATGGCTTGAATAAG  GAAATGACAATTTTT  TCCACTTATCTGATC
ARLV2  AATATCACAGAAAAG  CATGGCTTGAATAAG  GAAATGACAATTTTT  TCCACTTATCTGATC
ARL    AATATCACAGAAAAG  CATGGCTTGAATAAG  GAAATGACAATTTTT  TCCACTTATCTGATC
```

FIG.3H

```
       1261                                                                            1320
ARLV1  AGAACAAATGTTTAT TAAGCATCAGAAAACT CTGCCAACACTGAGG ATGTAAAGATCAATA
ARLV2  AGAACAAATGTTTAT TAAGCATCAGAAAACT CTGCCAACACTGAGG ATGTAAAGATCAATA
ARL    AGAACAAATGTTTAT TAAGCATCAGAAAACT CTGCCAACACTGAGG ATGTAAAGATCAATA

1321
ARLV1  AAAAAAATAATAATC AT   1090
ARLV2  AAAAAAATAATAATC AT   1279
ARL    AAAAAAATAATAATC AT   1337
```

FIG.4A

```
      1
ARLV1 MATFVELSTKAKMPI VGLGTWKSPLGKVKE AVKVAIDAGYRHIDC AYVYQNEHEVGEAIQ    60
ARLV2 MATFVELSTKAKMPI VGLGTWKSPLGKVKE AVKVAIDAGYRHIDC AYVYQNEHEVGEAIQ
ARL   MATFVELSTKAKMPI VGLGTWKSPLGKVKE AVKVAIDAGYRHIDC AYVYQNEHEVGEAIQ 61                                                              120
ARLV1 EKIQEKAVKREDLFI VSKLWPT-------- --------------- ---------------
ARLV2 EKIQEKAVKREDLFI VSKLWPTFFERPLVR KAFEKTLKDLKLSYL DVYLIHWPQGFKSGD
ARL   EKIQEKAVKREDLFI VSKLWPTFFERPLVR KAFEKTLKDLKLSYL DVYLIHWPQGFKSGD 121                                                             180
ARLV1 --------------- --------------- --------------- ---------------
ARLV2 DLFPKDDKGNAIGGK ATFLDAWEAMEELVD EGLVKALGVSNFSHF QIEKLLNKPGLKYKP
ARL   DLFPKDDKGNAIGGK ATFLDAWEAMEELVD EGLVKALGVSNFSHF QIEKLLNKPGLKYKP
```

FIG.4B

```
        181
ARLV1   ---------- ---------- ---------- ---------- ---------- ----------   240
ARLV2   ---------- VTNQVECHPY LTQEK      LIQYCHSKGI TVTAY      SPLGSPDRPW AKPED      PSLLEDPKIK EIAAK
ARL                VTNQVECHPY LTQEK      LIQYCHSKGI TVTAY      SPLGSPDRPW AKPED      PSLLEDPKIK EIAAK

241
ARLV1   ---------- ---------- ---------- ---------- ---------- ----------   300
ARLV2   H--------- ---------- ---------- ---------- ---------- ----------
ARL     HKKTAAQVLI RFHIQ      RNVIVIPKSV TPARI      VENIQVFDFK LSDEE      MATILSFNRN WRACN

301
ARLV1   ---------- ---SRSRSS  88
ARLV2   ---------- ---SPSL--  245
ARL     VLQSSHLEDY PFDAE      Y-----     316
```

HUMAN ARL-RELATED GENE VARIANTS ASSOCIATED WITH CANCERS

FIELD OF THE INVENTION

The invention relates to the nucleic acid sequences of two novel human ARL-related gene variants (ARLV1 and ARLV2) and the polypeptides encoded thereby, the preparation process thereof, and the uses of the same in diagnosing diseases associated with the gene variants, in particular human cancers, e.g., large cell lung cancer or hepatocellular carcinoma.

BACKGROUND OF THE INVENTION

Lung cancer is one of the major causers of cancer-related deaths in the world. There are two primary types of lung cancers: small cell lung cancer (SCLC) and non-small cell lung cancer (NSCLC) (Carney, (1992a) Curr. Opin. Oncol. 4:292–8). Small cell lung cancer accounts for approximately 25% of lung cancer and spreads aggressively (Smyth et al. (1986) Q J Med. 61: 969–76; Carney, (1992b) Lancet 339: 843–6). Non-small cell lung cancer represents the majority (about 75%) of lung cancer, and is further divided into three main subtypes: squamous cell carcinoma, adenocarcinoma, and large cell carcinoma (Ihde and Minutesna, (1991) Cancer 15: 105–54). In recent years, much progress has been made toward understanding the molecular and cellular biology of lung cancers. Many important contributions have been made by the identification of several key genetic factors associated with lung cancers. However, the treatments of lung cancers still mainly depend on surgery, chemotherapy, and radiotherapy. This is because the molecular mechanisms underlying the pathogenesis of lung cancers remain largely unclear.

A recent hypothesis suggests that lung cancer is caused by genetic mutations of at least 10 to 20 genes (Sethi, (1997) BMJ. 314: 652–655). Therefore, future strategies for the prevention and treatment of lung cancers will be focused on the elucidation of these genetic substrates, in particular, the genes responsible for detoxifying metabolites produced by cancer cells. Recently, a novel human aldose reductase-like gene (ARL-1; GenBank accession # U37100) was reported to be over-expressed in liver cancers and suggested to play a role in detoxifying metabolites generated by cancer cells (Cao et al. (1998) J. Biol. Chem. 273:11429–35). This suggests that the gene variants of this novel gene (we named it ARLV for the purpose of the present study) may be important targets for diagnostic markers of cancers.

SUMMARY OF THE INVENTION

The invention provides two ARL-related gene variants found in human large cell lung cancer, and the polypeptide sequences encoded thereby, which are useful in the diagnosis of the diseases associated with the deficiency of human ARL gene, in particular cancers, preferably large cell lung cancer or hepatocellular carcinoma.

The invention further provides expression vectors and host cells for expressing ARLV1 and ARLV2.

The invention further provides a method for producing the polypeptides encoded by ARLV1 and ARLV2.

The invention further provides antibodies specifically binding to the polypeptides encoded by ARLV1 and ARLV2.

The invention also provides methods for diagnosing the diseases associated with the deficiency of human ARL gene, in particular cancers, preferable large cell lung cancer or hepatocellular carcinoma.

BRIEF DESCRIPTION OF THE DRAWINGS

FIGS. 1A to 1C show the nucleic acid sequence of ARLV1 (SEQ ID NO:1) and the amino acid sequence encoded thereby (SEQ ID NO:2).

FIGS. 2A to 2C show the nucleic acid sequence of ARLV2 (SEQ ID NO:3) and the amino acid sequence encoded thereby (SEQ ID NO:4).

FIGS. 3A to 3H show the nucleotide sequence alignment between the human ARL gene (SEQ ID NO: 5) and ARL V1 (SEQ ID NO: 1) and ARL V2 (SEQ ID NO: 3).

FIGS. 4A to 4B show the amino acid sequence alignment between the human ARL polypeptide (SEQ ID NO: 6) and the polypeptides encoded by ARL V1 (SEQ ID NO: 2) and ARL V2 (SEQ ID NO: 4).

DETAILED DESCRIPTION OF THE INVENTION

According to the invention, all technical and scientific terms used have the same meanings as commonly understood by persons skilled in the art.

The term "antibody," as used herein, denotes intact molecules (a polypeptide or group of polypeptides) as well as fragments thereof, such as Fab, R(ab')$_2$, and Fv fragments, which are capable of binding the epitopic determinutesant. Antibodies are produced by specialized B cells after stimulation by an antigen. Structurally, antibody consists of four subunits, including two heavy chains and two light chains. The internal surface shape and charge distribution of the antibody binding domain are complementary to the features of an antigen. Thus, antibody can specifically act against the antigen in an immune response.

The term "base pair (bp)," as used herein, denotes nucleotides composed of a purine on one strand of DNA which can be hydrogen bonded to a pyrimidine on the other strand. Thymine (or uracil) and adenine residues are linked by two hydrogen bonds. Cytosine and guanine residues are linked by three hydrogen bonds.

The term "Basic Local Alignment Search Tool (BLAST; Altschul et al., (1997) Nucleic Acids Res. 25: 3389–3402)," as used herein, denotes programs for evaluation of homologies between a query sequence (amino or nucleic acid) and a test sequence as described by Altschul et al. (Nucleic Acids Res. 25: 3389–3402, 1997). Specific BLAST programs are described as follows:

(1) BLASTN compares a nucleotide query sequence against a nucleotide sequence database;

(2) BLASTP compares an amino acid query sequence against a protein sequence database;

(3) BLASTX compares the six-frame conceptual translation products of a query nucleotide sequence against a protein sequence database;

(4) TBLASTN compares a query protein sequence against a nucleotide sequence database translated in all six reading frames; and (5) TBLASTX compares the six-frame translations of a nucleotide query sequence against the six-frame translations of a nucleotide sequence database.

The term "cDNA," as used herein, denotes nucleic acids that synthesized from a mRNA template using reverse transcriptase.

The term "cDNA library," as used herein, denotes a library composed of complementary DNAs which are reverse-transcribed from mRNAs.

The term "complement," as used herein, denotes a polynucleotide sequence capable of forming base pairing with another polynucleotide sequence.

The term "deletion," as used herein, denotes a removal of a portion of one or more amino acid residues/nucleotides from a gene.

The term "expressed sequence tags (ESTs)," as used herein, denotes short (200 to 500 base pairs) nucleotide sequence that derives from either the 5' or 3' end of a cDNA.

The term "expression vector," as used herein, denotes nucleic acid constructs which contain a cloning site for introducing the DNA into a vector, one or more selectable markers for selecting vectors containing the DNA, an origin of replication for replicating the vector whenever the host cell divides, a terminator sequence, a polyadenylation signal, and a suitable control sequence which can effectively express the DNA in a suitable host. The suitable control sequence may include promoter, enhancer and other regulatory sequences necessary for directing polymerases to transcribe the DNA.

The term "host cell," as used herein, denotes a cell which is used to receive, maintain, and allow the reproduction of an expression vector comprising DNA. Host cells are transformed or transfected with suitable vectors constructed using recombinant DNA methods. The recombinant DNA introduced with the vector is replicated whenever the cell divides.

The term "insertion" or "addition," as used herein, denotes the addition of a portion of one or more amino acid residues/nucleotides to a gene.

The term "in silico," as used herein, denotes a process of using computational methods (e.g., BLAST) to analyze DNA sequences.

The term "polymerase chain reaction (PCR)," as used herein, denotes a method which increases the copy number of a nucleic acid sequence using a DNA polymerase and a set of primers (about 20–30 bp oligonucleotides complementary to each strand of DNA) under suitable conditions (successive rounds of primer annealing, strand elongation, and dissociation).

The term "primer," as used herein, denotes a single-stranded synthetic oligonucleotide designed to hybridize to a particular template DNA sequence. The forward primer is the one complementary to one strand at the 5'-end of the DNA sequence. The reverse primer is the one complementary to the other strand at the 3'-end of the DNA sequence.

The term "protein" or "polypeptide," as used herein, denotes a sequence of amino acids in a specific order that can be encoded by a gene or by a recombinant DNA. It can also be chemically synthesized.

The term "nucleic acid sequence" or "polynucleotide," as used herein, denotes a sequence of nucleotide (guanine, cytosine, thymine or adenine) in a specific order that can be a natural or synthesized fragment of DNA or RNA. It may be single-stranded or double-stranded.

The term "reverse transcriptase-polymerase chain reaction (RT-PCR)," as used herein, denotes a process which transcribes mRNA to complementary DNA strand using reverse transcriptase followed by polymerase chain reaction to amplify the specific fragment of DNA sequences.

The term "transformation," as used herein, denotes a process describing the uptake, incorporation, and expression of exogenous DNA by prokaryotic host cells.

The term "transfection," as used herein, a process describing the uptake, incorporation, and expression of exogenous DNA by eukaryotic host cells.

The term "variant," as used herein, denotes a fragment of sequence (nucleotide or amino acid) inserted or deleted by one or more nucleotides/amino acids.

In the first aspect, the subject invention provides the nucleotide sequences of ARLV1 and ARLV2, and the polypeptides encoded by these two novel human ARL-related gene variants and the fragments thereof.

According to the invention, human ARL cDNA sequence was used to query a human large cell lung cancer EST database using BLAST program to search for ARL-related gene variants. Two human cDNA partial sequences (i.e., ESTs) deposited in the databases showing similar to ARL were isolated and sequenced. These clones (named ARLV1 and ARLV2) were isolated. FIGS. 1 and 2 show the nucleic acid sequences (SEQ ID NOs: 1 and 3) of the variants (ARLV1 and ARLV2) and the corresponding amino acid sequences (SEQ ID NOs: 2 and 4) encoded thereby.

The full-length of the ARLV1 cDNA is a 1090 bp clone containing a 264 bp open reading frame (ORF) extending from nucleotides 70 to 333, which corresponds to an encoded protein of 88 amino acid residues with a predicted molecular mass of 9.9 kDa. The full-length of the ARLV2 cDNA is a 1279 bp clone containing a 735 bp ORF extending from nucleotides 70 to 804, which corresponds to an encoded protein of 245 amino acid residues with a predicted molecular mass of 27.7 kDa. To determine the variations (insertion/deletion) in sequences of ARLV1 and ARLV2 cDNA clones, alignments of the nucleotide sequences and the amino acid sequences between ARL, ARLV1 and ARLV2 were preformed (FIGS. 3 and 4). The results indicate that two genetic deletions were found in the aligned sequences. This information demonstrates that ARLV1 has a 247 bp deletion in the sequence of ARL from nucleotides 317–563 and ARLV2 has a 58 bp deletion in the sequence of ARL from nucleotides 793–850.

In the invention, a search of ESTs deposited in dbEST (Boguski et al., (1993) Nat Genet. 4: 332–3) at NCBI was performed. Four ESTs were found to confirm the missing region described in ARLV1 and ARLV2. One EST (GenBank accession number BQ221381), confirmed the absence of the 247 bp region on ARLV1 nucleotide sequence, was found to be isolated from a large cell lung cancer cDNA library. This suggests that the absence of the 247 bp nucleotide fragment located between nucleotides 316–317 of ARLV1 may be a useful marker for large cell lung cancer diagnosis. Three ESTs (GenBank accession numbers AV683595, AV698712, AV691243), confirmed the absence of the 58 bp region on ARLV2 nucleotide sequences, were found to be isolated from a hepatocellular carcinoma cDNA library. This suggests that the absence of the 58 bp nucleotide fragment located between nucleotides 792–793 of ARLV2 may be a useful marker for hepatocellular carcinoma diagnosis.

Therefore, any nucleotide fragments comprising nucleotides 314–319, preferably nucleotides 304–333 of ARLV1, or nucleotides 790–795, preferably nucleotides 775–804 of ARLV2, may be used as probes for determining the presence of the variants under highly stringent conditions. An alternative approach is that any set of primers for amplifying the fragment containing nucleotides 314–319, preferably nucleotides 304–333 of ARLV1, or nucleotides 790–795, preferably nucleotides 775–804 of ARLV2, may be used for determining the presence of the variants.

According to the present invention, the polypeptides encoded by human ARL-related gene variants (ARLV1 and ARLV2) and fragments thereof may be produced through genetic engineering techniques. In this case, they are produced by appropriate host cells that have been transformed by DNAs that code the polypeptides or fragments thereof. The nucleotide sequence encoding the polypeptide of the human ARL-related gene variants or fragment thereof is inserted into an appropriate expression vector, i.e., a vector which contains the necessary elements for the transcription and translation of the inserted coding sequence in a suitable host. The nucleic acid sequence is inserted into the vector in a manner that it will be expressed under appropriate conditions (e.g., in proper orientation and correct reading frame, and with appropriate expression sequences, including an RNA polymerase binding sequence and a ribosomal binding sequence).

Any method that is known to those skilled in the art may be used to construct expression vectors containing the sequences encoding the polypeptides of the human ARL-related gene variants and appropriate transcriptional/translational control elements. These methods may include in vitro recombinant DNA and synthetic techniques, and in vivo genetic recombinants. (See, e.g., Sambrook, J. Cold Spring Harbor Press, Plainview N.Y., ch. 4, 8, and 16–17; Ausubel, R. M. et al. (1995) Current protocols in Molecular Biology, John Wiley & Sons, New York N.Y., ch. 9, 13, and 16.)

A variety of expression vector/host systems may be utilized to express the polypeptide-coding sequence. These include, but are not limited to, microorganisms such as bacteria transformed with recombinant bacteriophage, plasmid, or cosmid DNA expression vector; yeast transformed with yeast expression vector; insect cell systems infected with virus (e.g., baculovirus); plant cell system transformed with viral expression vector (e.g., cauliflower mosaic virus, CaMV, or tobacco mosaic virus, TMV); or animal cell system infected with virus (e.g., vaccina virus, adenovirus, etc.). Preferably, the host cell is a bacterium, and most preferably, the bacterium is $E.$ $coli$.

Alternatively, the polypeptides encoded by human ARL-related gene variants or fragments thereof may be synthesized using chemical methods. For example, peptide synthesis can be performed using various solid-phase techniques (Roberge, J. Y. et al. (1995) Science 269: 202 to 204). Automated synthesis may be achieved using the ABI 431A peptide synthesizer (Perkin-Elmer).

According to the present invention, the fragments of the polypeptides and nucleic acid sequences of the human ARL-related gene variants are used as immunogens and primers or probes, respectively. It is preferable to use the purified fragments of the human ARL-related gene variants. The fragments may be produced by enzyme digestion, chemical cleavage of isolated or purified polypeptide or nucleic acid sequences, or chemical synthesis and then may be isolated or purified. Such isolated or purified fragments of the polypeptides and nucleic acid sequences can be used directly as immunogens and primers or probes, respectively.

The present invention further provides the antibodies which specifically bind one or more out-surface epitopes of the polypeptides encoded by human ARL-related gene variants.

According to the present invention, immunization of mammals with immunogens described herin, preferably humans, rabbits, rats, mice, sheep, goats, cows, or horses, is performed following procedures well known to those skilled in the art, for the purpose of obtaining antisera containing polyclonal antibodies or hybridoma lines secreting monoclonal antibodies.

Monoclonal antibodies can be prepared by standard techniques, given the teachings contained herein. Such techniques are disclosed, for example, in U.S. Pat. No. 4,271,145 and U.S. Pat. No. 4,196,265. Briefly, an animal is immunized with the immunogen. Hybridomas are prepared by fusing spleen cells from the immunized animal with myeloma cells. The fusion products are screened for those producing antibodies that bind to the immunogen. The positive hybridoma clones are isolated, and the monoclonal antibodies are recovered from those clones.

Immunization regimens for production of both polyclonal and monoclonal antibodies are well-known in the art. The immunogen may be injected by any of a number of routes, including subcutaneous, intravenous, intraperitoneal, intradermal, intramuscular, mucosal, or a combination thereof. The immunogen may be injected in soluble form, aggregate form, attached to a physical carrier, or mixed with an adjuvant, using methods and materials well-known in the art. The antisera and antibodies may be purified using column chromatography methods well known to those skilled in the art.

According to the present invention, antibody fragments which contain specific binding sites for the polypeptides or fragments thereof may also be generated. For example, such fragments include, but are not limited to, $F(ab')_2$ fragments produced by pepsin digestion of the antibody molecule and Fab fragments generated by reducing the disulfide bridges of the $F(ab')_2$ fragments.

Many gene variants have been found to be associated with diseases (Stallings-Mann et al., (1996) Proc Natl Acad Sci USA 93: 12394–9; Liu et al., (1997) Nat Genet 16:328–9; Siffert et al., (1998) Nat Genet 18: 45 to 8; Lukas et al., (2001) Cancer Res 61: 3212 to 9). Based on the cDNA libraries of the matched ESTs, ARLV1 and ARLV2 can be specifically associated with large cell lung cancer and hepatocellular carcinoma, respectively. Thus, the expression level of ARLV1 and ARLV2 each relative to ARL may be a useful indicator for screening of patients suspected of having cancers, or more specifically, the large cell lung cancer or hepatocellular carcinoma. This suggests that the index of relative expression level (mRNA or protein) may associate with an increased susceptibility to cancers, more preferably, large cell lung cancer or hepatocellular carcinoma. Fragments of ARLV1 and ARLV2 transcripts (mRNAs) may be detected by RT-PCR approach. Polypeptides encoded by the ARL-related gene variants may be determined by the binding of antibodies to these polypeptides. These approaches may be performed in accordance with conventional methods well known by persons skilled in the art.

The subject invention also provides methods for diagnosing the diseases associated with the deficiency of human ARL gene in a mammal, in particular, large cell lung cancer or hepatocellular carcinoma.

The method for diagnosing the diseases associated with the deficiency of human ARL gene may be performed by detecting the presence of the nucleotide sequences of ARLV1 and ARLV2 of the invention, which comprises the steps of: (1) extracting total RNA of cells obtained from a mammal; (2) amplifying the RNA by reverse transcriptase-polymerase chain reaction (RT-PCR) with a set of primers to obtain a cDNA comprising the fragments comprising nucleotides 314–319, preferably nucleotides 304–333 of SEQ ID NO: 1 or nucleotides 790–795, preferably nucleotides 775–804 of SEQ ID NO: 3; and (3) detecting whether the cDNA sample is obtained. If necessary, the amount of the obtained cDNA sample may be detected.

In this embodiment, a forward primer may be designed to have a sequence comprising nucleotides 314–319, preferably nucleotides 304–333 of SEQ ID NO: 1, and a reverse primer may be designed to have a sequence complementary to the nucleotides of SEQ ID NO: 1 at any other locations downstream of nucleotide 319, preferably nucleotide 333; or a forward primer has a sequence comprising nucleotides 790–795, preferably nucleotides 775–804 of SEQ ID NO: 3, and a reverse primer has a sequence complementary to the nucleotides of SEQ ID NO: 3 at any other locations downstream of nucleotide 795, preferably nucleotide 804. Alternatively, the reverse primer may be designed to have a sequence complementary to the nucleotides of SEQ ID NO: 1 containing nucleotides 314–319, preferably nucleotides 304–333, and the forward primer may be designed to have a sequence comprising the nucleotides of SEQ ID NO: 1 at any other locations upstream of nucleotide 314, preferably nucleotide 304; or the reverse primer has a sequence complementary to the nucleotides of SEQ ID NO: 3 containing nucleotides 790–795, preferably nucleotides 775–804, and the forward primer has a sequence comprising the nucleotides of SEQ ID NO: 3 at any other locations upstream of nucleotide 790, preferably nucleotide 775. In this case, only ARLV1 and ARLV2 will be amplified.

Alternatively, the forward primer may be designed to have a sequence comprising the nucleotides of SEQ ID NO: 1 at any locations upstream of nucleotide 314 and the reverse primer may be designed to have a sequence complementary to the nucleotides of SEQ ID NO: 1 at any other locations downstream of nucleotide 319; or the forward primer has a sequence comprising the nucleotides of SEQ ID NO: 3 at any locations upstream of nucleotide 790 and the reverse primer has a sequence complementary to the nucleotides of SEQ ID NO: 3 at any other locations downstream of nucleotide 795. In this case, ARLV1 or ARLV2 together with ARL in a sample will be amplified. The length of the PCR fragment from ARLV1 will be 247 bp shorter than that from ARL; the length of the PCR fragment from ARLV2 will be 58 bp shorter than that from ARL.

Preferably, the primers of the invention contain 20 to 30 nucleotides.

Total RNA may be isolated from patient samples by using TRIZOL reagents (Life Technology). Tissue samples (e.g., biopsy samples) are powdered under liquid nitrogen before homogenization. RNA purity and integrity are assessed by absorbance at 260/280 nm and by agarose gel electrophoresis. The set of primers designed to amplify the expected sizes of specific PCR fragments of gene variants (ARLV1 and ARLV2) can be used. PCR fragments are analyzed on a 1% agarose gel using five microliters (10%) of the amplified products. The intensity of the signals may be determined by using the Molecular Analyst program (version 1.4.1; Bio-Rad). Thus, the index of relative expression levels for each co-amplified PCR products may be calculated based on the intensity of signals.

The RT-PCR experiment may be performed according to the manufacturer instructions (Boehringer Mannheim). A 50 µl reaction mixture containing 2 µl total RNA (0.1 µg/µl), 1 µl each primer (20 pM), 1 µeach dNTP (10 mM), 2.5 µl DTT solution (100 mM), 10 µl 5×RT-PCR buffer, 1 µl enzyme mixture, and 28.5 µl sterile distilled water may be subjected to the conditions such as reverse transcription at 60° C. for 30 minutes followed by 35 cycles of denaturation at 94° C. for 2 minutes, annealing at 60° C. for 2 minutes, and extension at 68° C. for 2 minutes. The RT-PCR analysis may be repeated twice to ensure reproducibility, for a total of three independent experiments.

Another embodiment of the method for diagnosing the diseases associated with the deficiency of human ARL gene is performed by detecting the nucleotide sequence of ARLV1 or ARLV2, which comprises the steps of: (1) extracting total RNA from a sample obtained from the mammal; (2) amplifying the RNA by reverse transcriptase-polymerase chain reaction (RT-PCR) to obtain a cDNA sample; (3) bringing the cDNA sample into contact with the nucleic acid selected from the group consisting of SEQ ID NOs: 1 and 3, and the fragments thereof; and (4) detecting whether the cDNA sample hybridizes with the nucleic acid of SEQ ID NOs: 1 or 3, or the fragments thereof. If necessary, the amount of hybridized sample may be detected.

The expression of gene variants can be analyzed using Northern Blot hybridization approach. Specific fragment which comprising nucleotides 314–319, preferably nucleotides 304–333 of the ARLV1 or nucleotides 790–795, preferably nucleotides 775–804 of the ARLV2 may be amplified by polymerase chain reaction (PCR) using primer set designed for RT-PCR. The amplified PCR fragment may be labeled and serve as a probe to hybridize the membranes containing total RNAs extracted from the samples under the conditions of 55° C. in a suitable hybridization solution for 3 hours. Blots may be washed twice in 2×SSC, 0.1% SDS at room temperature for 15 minutes each, followed by two washes in 0.1×SSC and 0.1% SDS at 65° C. for 20 minutes each. After these washes, the blots may be rinsed briefly in a suitable washing buffer and incubated in blocking solution for 30 minutes, and then incubated in a suitable antibody solution for 30 minutes. Blots may be washed in washing buffer for 30 minutes and equilibrated in suitable detection buffer before detecting the signals. Alternatively, the presence of gene variants (cDNAs or PCR) can be detected using the microarray approach. The cDNAs or PCR products corresponding to the nucleotide sequences of the present invention may be immobilized on a suitable substrate such as a glass slide. Hybridization can be preformed using the labeled mRNAs extracted from samples. After hybridization, nonhybridized mRNAs are removed. The relative abundance of each labeled transcript, hybridizing to a cDNA/PCR product immobilized on the microarray, can be determined by analyzing the scanned images.

According to the present invention, the method for diagnosing the diseases associated with the deficiency of human ARL gene may also be performed by detecting the polypeptides encoded by ARLV1 and ARLV2 of the invention. For instance, the polypeptides in protein samples obtained from the mammal may be determined by, but is not limited to, the immunoassay wherein the antibody specifically binding to the polypeptides of the invention is contacted with the protein sample, and the antibody-polypeptide complex is detected. If necessary, the amount of the antibody-polypeptide complexes can be determined.

The polypeptides encoded by the gene variants may be expressed in prokaryotic cells by using suitable prokaryotic expression vectors. The cDNA fragments of ARLV1 or ARLV2 genes encoding the amino acid coding sequence may be PCR amplified with restriction enzyme digestion sites incorporated in the 5' and 3' ends, respectively. For example, specific fragments which comprise nucleotides 304–333 (encoding amino acid residues 79–88) of the ARLV1 or nucleotides 775–804 (encoding amino acid residues 236–245) of the ARLV2 may be PCR amplified. The PCR products can then be enzyme digested, purified, and inserted into the corresponding sites of prokaryotic expression vector in-frame to generate recombinant plasmids. Sequence fidelity of this recombinant DNA can be verified by sequencing. The prokaryotic recombinant plasmids may be transformed into host cells (e.g., *E. coli* BL21 (DE3)).

Recombinant protein synthesis may be stimulated by the addition of 0.4 mM isopropylthiogalactoside (IPTG) for 3 hours. The bacterially-expressed proteins may be purified.

The polypeptides encoded by ARL-related gene variants may be expressed in animal cells by using eukaryotic expression vectors. Cells may be maintained in Dulbecco's modified Eagle's medium (DMEM) supplemented with 10% fetal bovine serum (FBS; Gibco BRL) at 37° C. in a humidified 5% $CO_2$ atmosphere. Before transfection, the nucleotide sequence of each of the gene variant may be amplified with PCR primers containing restriction enzyme digestion sites and ligated into the corresponding sites of eukaryotic expression vector in-frame. Sequence fidelity of this recombinant DNA can be verified by sequencing. The cells may be plated in 12-well plates one day before transfection at a density of $5\times10^4$ cells per well. Transfections may be carried out using Lipofectamine Plus transfection reagent according to the manufacturer's instructions (Gibco BRL). Three hours following transfection, medium containing the complexes may be replaced with fresh medium. Forty-eight hours after incubation, the cells may be scraped into lysis buffer (0.1 M Tris HCl, pH 8.0, 0.1% Triton X-100) for purification of expressed proteins/polypeptides. After these proteins/polypeptides are purified, monoclonal antibodies against these purified proteins/polypeptides (ARLV1 and ARLV2) may be generated using hybridoma technique according to the conventional methods (de StGroth and Scheidegger, (1980) J Immunol Methods 35:1–21; Cote et al. (1983) Proc Natl Acad Sci USA 80: 2026–30; and Kozbor et al. (1985) J Immunol Methods 81:31–42).

According to the present invention, the presence of the polypeptides encoded by the gene variants in samples of lung cancers may be determined by, but is not limited to, Western blot analysis. Proteins extracted from samples may be separated by SDS-PAGE and transferred to suitable membranes such as polyvinylidene difluoride (PVDF) in transfer buffer (25 mM Tris-HCl, pH 8.3, 192 mM glycine, 20% methanol) with a Trans-Blot apparatus for 1 hour at 100 V (e.g., Bio-Rad). The proteins can be immunoblotted with specific antibodies. For example, membrane blotted with extracted proteins may be blocked with suitable buffers such as 3% solution of BSA or 3% solution of nonfat milk powder in TBST buffer (10 mM Tris-HCl, pH 8.0, 150 mM NaCl, 0.1% Tween 20) and incubated with monoclonal antibody directed against the polypeptides encoded by the gene variants. Unbound antibody is removed by washing with TBST for 5×1 minutes. Bound antibody may be detected using commercial ECL Western blotting detecting reagents.

The following examples are provided for illustration, but not for limiting the invention.

EXAMPLES

Analysis of Human Lung EST Databases

Expressed sequence tags (ESTs) generated from the large-scale PCR-based sequencing of the 5'-end of human clones from a large cell lung cancer cDNA library were compiled and served as an EST database. Sequence comparisons against the nonredundant nucleotide and protein databases were performed using BLASTN and BLASTX programs (Altschul et al., (1997) Nucleic Acids Res. 25: 3389–3402; Gish and States, (1993) Nat Genet 3:266–272), at the National Center for Biotechnology Information (NCBI) with a significance cutoff of $p<10^{-10}$. ESTs representing putative ARL encoding gene were identified during the course of EST generation.

Isolation of cDNA Clones

Two cDNA clones exhibiting EST sequences similar to the ARL gene were isolated from the cDNA library and named ARLV1 and ARLV2. The inserts of these clones were subsequently excised in vivo from the λZAP Express vector using the ExAssist/XLOLR helper phage system (Stratagene). Phagemid particles were excised by coinfecting XL1-BLUE MRF' cells with ExAssist helper phage. The excised pBluescript phagemids were used to infect E. Coli XLOLR cells, which lack the amber suppressor necessary for ExAssist phage replication. Infected XLOLR cells were selected using kanamycin resistance. Resultant colonies contained the double stranded phagemid vector with the cloned cDNA insert. A single colony was grown overnight in LB-kanamycin, and DNA was purified using a Qiagen plasmid purification kit.

Full Length Nucleotide Sequencing and Database Comparisons

Phagemid DNA was sequenced using the Epicentre#SE9101LC SequiTherm EXCEL™II DNA Sequencing Kit for 4200S-2 Global NEW $IR^2$ DNA sequencing system (LI-COR). Using the primer-walking approach, full-length sequence was determined. Nucleotide and protein searches were performed using BLAST against the non-redundant database of NCBI.

In Silico Tissue Distribution Analysis

The coding sequence for each cDNA clones was searched against the dbEST sequence database (Boguski et al., (1993) Nat Genet. 4: 332–3) using the BLAST algorithm at the NCBI website. ESTs derived from each tissue were used as a source of information for transcript tissue expression analysis. Tissue distribution for each isolated cDNA clone was determined by ESTs matching to the particular sequence variants (insertions or deletions) with a significance cutoff of $p<10^{-10}$.

REFERENCES

Altschul et al., Gapped BLAST and PSI-BLAST: a new generation of protein database search programs, Nucleic Acids Res, 25: 3389–3402, (1997).

Ausubel et al., Current protocols in Molecular Biology, John Wiley & Sons, New York N.Y., ch. 9, 13, and 16, (1995).

Boguski et al., dbEST—database for "expressed sequence tags". Nat Genet. 4: 332–3, (1993).

Cao et al., Identification and characterization of a novel human aldose reductase-like gene, J. Biol. Chem. 273: 11429–35, (1998)

Cao et al., Nucleotide Accession No. U37100

Carney, D. N. The biology of lung cancer. Curr. Opin. Oncol. 4: 292–8, (1992a).

Carney, D. N. Biology of small-cell lung cancer. Lancet 339: 843–6, (1992b).

Cote et al., Generation of human monoclonal antibodies reactive with cellular antigens, Proc Natl Acad Sci U S A 80: 2026–30, (1983).

de StGroth and Scheidegger, Production of monoclonal antibodies: strategy and tactics, J Immunol Methods 35:1–21, (1980).

Gish and States, Identification of protein coding regions by database similarity search, Nat Genet, 3:266–272, (1993).

Han, Z. EST Accession No. AV683595, AV698712, AV691243

Ihde and Minna, Non-small cell lung cancer. Part II: Treatment. Curr. Probl. Cancer 15: 105–54, (1991).

Kozbor et al., Specific immunoglobulin production and enhanced tumorigenicity following ascites growth of human hybridomas, J Immunol Methods, 81:31–42 (1985).

Liu et al., Silent mutation induces exon skipping of fibrillin-1 gene in Marfan syndrome. Nat Genet 16:328–9, (1997).

Lukas et al., Alternative and aberrant messenger RNA splicing of the mdm2 oncogene in invasive breast cancer. Cancer Res 61:3212–9, (2001).

Roberge et al., A strategy for a convergent synthesis of N-linked glycopeptides on a solid support. Science 269: 202–4, (1995).

Sambrook, J. Cold Spring Harbor Press, Plainview N.Y., ch. 4, 8, and 16–17.

Sethi, Science, medicine, and the future. Lung cancer, BMJ, 314: 652–655, (1997)

Siffert et al., Association of a human G-protein beta3 subunit variant with hypertension. Nat Genet, 18:45–8, (1998).

Smyth et al., The impact of chemotherapy on small cell carcinoma of the bronchus. Q J Med, 61: 969–76, (1986).

Stallings-Mann et al., Alternative splicing of exon 3 of the human growth hormone receptor is the result of an unusual genetic polymorphism. Proc Natl Acad Sci U S A 93:12394–9, (1996).

Strausberg, R. EST Accession No. BQ221381

What is claimed is:

1. An isolated nucleic acid comprising the nucleotide sequence of SEQ ID NO: 1.

2. An isolated nucleic acid comprising nucleotides 304 to 333 of SEQ ID NO: 1.

3. An expression vector comprising the nucleic acid of claim 1.

4. An isolated host cell transformed with the expression vector of claim 3.

5. A method for producing a polypeptide, which comprises the steps of:
   (1) culturing the host cell of claim 4 under a condition suitable for the expression of the polypeptide; and
   (2) recovering the polypeptide from the host cell culture.

* * * * *

SEQUENCE LISTING

```
<160> NUMBER OF SEQ ID NOS: 4

<210> SEQ ID NO 1
<211> LENGTH: 1090
<212> TYPE: DNA
<213> ORGANISM: ARTIFICIAL SEQUENCE
<220> FEATURE:
<223> OTHER INFORMATION: VARIANT OF HUMAN ALDOSE REDUCTASE-LIKE GENE
<220> FEATURE:
<221> NAME/KEY: CDS
<222> LOCATION: (70)..(333)

<400> SEQUENCE: 1
caaaaacagc aacagaaagc aggacgtgag acttctacct gctcactcag aatcatttct      60 gcaccaacc atg gcc acg ttt gtg gag ctc agt acc aaa gcc aag atg ccc     111
          Met Ala Thr Phe Val Glu Leu Ser Thr Lys Ala Lys Met Pro
          1               5                  10 att gtg ggc ctg ggc act tgg aag tct cct ctc ggc aaa gtg aaa gaa      159
Ile Val Gly Leu Gly Thr Trp Lys Ser Pro Leu Gly Lys Val Lys Glu
15              20                  25                  30 gca gtg aag gtg gcc att gat gca gga tat cgg cac att gac tgt gcc      207
Ala Val Lys Val Ala Ile Asp Ala Gly Tyr Arg His Ile Asp Cys Ala
                35                  40                  45 tat gtc tat cag aat gaa cat gaa gtg ggg gaa gcc atc caa gag aag      255
Tyr Val Tyr Gln Asn Glu His Glu Val Gly Glu Ala Ile Gln Glu Lys
            50                  55                  60 atc caa gag aag gct gtg aag cgg gag gac ctg ttc atc gtc agc aag      303
Ile Gln Glu Lys Ala Val Lys Arg Glu Asp Leu Phe Ile Val Ser Lys
        65                  70                  75 ttg tgg ccc act tcc aga tcg aga agc tct tgaacaaacc tggactgaaa        353
Leu Trp Pro Thr Ser Arg Ser Arg Ser Ser
    80                  85 tataaaccag tgactaacca ggttgagtgt cacccatacc tcacgcagga gaaactgatc   413
cagtactgcc actccaaggg catcaccgtt acggcctaca gcccctggg ctctccggat    473 agaccttggg ccaagccaga agaccttcc ctgctggagg atcccaagat taaggagatt    533
gctgcaaagc acaaaaaaac cgcagcccag gttctgatcc gtttccatat ccagaggaat   593
gtgattgtca tccccaagtc tgtgacacca gcacgcattg ttgagaacat tcaggtcttt   653
gactttaaat tgagtgatga ggagatggca accatactca gcttcaacag aaactggagg   713
```

```
gcctgtaacg tgttgcaatc ctctcatttg gaagactatc ccttcgatgc agaatattga    773
ggttgaatct cctggtgaga ttatacagga gattctcttt cttcgctgaa gtgtgactac    833
ctccactcat gtcccatttt agccaagctt atttaagatc acagtgaact tagtcctgtt    893
atagacgaga atcgaggtgc tgttttagac atttatttct gtatgttcaa ctaggatcag    953
aatatcacag aaaagcatgg cttgaataag gaaatgacaa ttttttccac ttatctgatc   1013
agaacaaatg tttattaagc atcagaaact ctgccaacac tgaggatgta aagatcaata   1073
aaaaaaataa taatcat                                                   1090

<210> SEQ ID NO 2
<211> LENGTH: 88
<212> TYPE: PRT
<213> ORGANISM: ARTIFICIAL SEQUENCE
<220> FEATURE:
<223> OTHER INFORMATION: PEPTIDE ENCODED BY VARIANT OF HUMAN ALDOSE
      REDUCTASE-LIKE GENE

<400> SEQUENCE: 2

Met Ala Thr Phe Val Glu Leu Ser Thr Lys Ala Lys Met Pro Ile Val
 1               5                  10                  15

Gly Leu Gly Thr Trp Lys Ser Pro Leu Gly Lys Val Lys Glu Ala Val
            20                  25                  30

Lys Val Ala Ile Asp Ala Gly Tyr Arg His Ile Asp Cys Ala Tyr Val
        35                  40                  45

Tyr Gln Asn Glu His Glu Val Gly Glu Ala Ile Gln Glu Lys Ile Gln
    50                  55                  60

Glu Lys Ala Val Lys Arg Glu Asp Leu Phe Ile Val Ser Lys Leu Trp
65                  70                  75                  80

Pro Thr Ser Arg Ser Arg Ser Ser
                85

<210> SEQ ID NO 3
<211> LENGTH: 1279
<212> TYPE: DNA
<213> ORGANISM: ARTIFICIAL SEQUENCE
<220> FEATURE:
<223> OTHER INFORMATION: VARIANT OF HUMAN ALDOSE REDUCTASE-LIKE GENE
<220> FEATURE:
<221> NAME/KEY: CDS
<222> LOCATION: (70)..(804)

<400> SEQUENCE: 3
caaaaacagc aacagaaagc aggacgtgag acttctacct gctcactcag aatcatttct     60 gcaccaacc atg gcc acg ttt gtg gag ctc agt acc aaa gcc aag atg ccc    111
           Met Ala Thr Phe Val Glu Leu Ser Thr Lys Ala Lys Met Pro
            1               5                  10 att gtg ggc ctg ggc act tgg aag tct cct ctc ggc aaa gtg aaa gaa      159
Ile Val Gly Leu Gly Thr Trp Lys Ser Pro Leu Gly Lys Val Lys Glu
 15                  20                  25                  30 gca gtg aag gtg gcc att gat gca gga tat cgg cac att gac tgt gcc      207
Ala Val Lys Val Ala Ile Asp Ala Gly Tyr Arg His Ile Asp Cys Ala
                 35                  40                  45 tat gtc tat cag aat gaa cat gaa gtg ggg gaa gcc atc caa gag aag      255
Tyr Val Tyr Gln Asn Glu His Glu Val Gly Glu Ala Ile Gln Glu Lys
         50                  55                  60 atc caa gag aag gct gtg aag cgg gag gac ctg ttc atc gtc agc aag      303
Ile Gln Glu Lys Ala Val Lys Arg Glu Asp Leu Phe Ile Val Ser Lys
     65                  70                  75
```

| | | | | | | | | | | | | | | | |
|---|---|---|---|---|---|---|---|---|---|---|---|---|---|---|---|
| ttg | tgg | ccc | act | ttc | ttt | gag | aga | ccc | ctt | gtg | agg | aaa | gcc | ttt | gag | 351
| Leu | Trp | Pro | Thr | Phe | Phe | Glu | Arg | Pro | Leu | Val | Arg | Lys | Ala | Phe | Glu |
| | 80 | | | | | 85 | | | | 90 | | | | | |

```
ttg tgg ccc act ttc ttt gag aga ccc ctt gtg agg aaa gcc ttt gag    351
Leu Trp Pro Thr Phe Phe Glu Arg Pro Leu Val Arg Lys Ala Phe Glu
     80                  85                  90 aag acc ctc aag gac ctg aag ctg agc tat ctg gac gtc tat ctt att    399
Lys Thr Leu Lys Asp Leu Lys Leu Ser Tyr Leu Asp Val Tyr Leu Ile
 95             100                 105                 110 cac tgg cca cag gga ttc aag tct ggg gat gac ctt ttc ccc aaa gat    447
His Trp Pro Gln Gly Phe Lys Ser Gly Asp Asp Leu Phe Pro Lys Asp
                115                 120                 125 gat aaa ggt aat gcc atc ggt gga aaa gca acg ttc ttg gat gcc tgg    495
Asp Lys Gly Asn Ala Ile Gly Gly Lys Ala Thr Phe Leu Asp Ala Trp
            130                 135                 140 gag gcc atg gag gag ctg gtg gat gag ggg ctg gtg aaa gcc ctt ggg    543
Glu Ala Met Glu Glu Leu Val Asp Glu Gly Leu Val Lys Ala Leu Gly
        145                 150                 155 gtc tcc aat ttc agc cac ttc cag atc gag aag ctc ttg aac aaa cct    591
Val Ser Asn Phe Ser His Phe Gln Ile Glu Lys Leu Leu Asn Lys Pro
    160                 165                 170 gga ctg aaa tat aaa cca gtg act aac cag gtt gag tgt cac cca tac    639
Gly Leu Lys Tyr Lys Pro Val Thr Asn Gln Val Glu Cys His Pro Tyr
175                 180                 185                 190 ctc acg cag gag aaa ctg atc cag tac tgc cac tcc aag ggc atc acc    687
Leu Thr Gln Glu Lys Leu Ile Gln Tyr Cys His Ser Lys Gly Ile Thr
                195                 200                 205 gtt acg gcc tac agc ccc ctg ggc tct ccg gat aga cct tgg gcc aag    735
Val Thr Ala Tyr Ser Pro Leu Gly Ser Pro Asp Arg Pro Trp Ala Lys
            210                 215                 220 cca gaa gac cct tcc ctg ctg gag gat ccc aag att aag gag att gct    783
Pro Glu Asp Pro Ser Leu Leu Glu Asp Pro Lys Ile Lys Glu Ile Ala
        225                 230                 235 gca aag cac tcc cca agt ctg tgacaccagc acgcattgtt gagaacattc       834
Ala Lys His Ser Pro Ser Leu
    240                 245 aggtctttga ctttaaattg agtgatgagg agatggcaac catactcagc ttcaacagaa   894
actggagggc ctgtaacgtg ttgcaatcct ctcatttgga agactatccc ttcgatgcag  954
aatattgagg ttgaatctcc tggtgagatt atacaggaga ttctctttct tcgctgaagt 1014 gtgactacct ccactcatgt cccatttta ccaagcttat ttaagatcac agtgaactta  1074
gtcctgttat agacgagaat cgaggtgctg ttttagacat ttatttctgt atgttcaact 1134 aggatcagaa tatcacagaa aagcatggct tgaataagga aatgacaatt ttttccactt 1194 atctgatcag aacaaatgtt tattaagcat cagaaactct gccaacactg aggatgtaaa 1254 gatcaataaa aaaaataata atcat                                       1279
```

<210> SEQ ID NO 4
<211> LENGTH: 245
<212> TYPE: PRT
<213> ORGANISM: ARTIFICIAL SEQUENCE
<220> FEATURE:
<223> OTHER INFORMATION: PEPTIDE ENCODED BY VARIANT OF HUMAN ALDOSE
      REDUCTASE-LIKE GENE

<400> SEQUENCE: 4

```
Met Ala Thr Phe Val Glu Leu Ser Thr Lys Ala Lys Met Pro Ile Val
 1               5                  10                  15

Gly Leu Gly Thr Trp Lys Ser Pro Leu Gly Lys Val Lys Glu Ala Val
            20                  25                  30

Lys Val Ala Ile Asp Ala Gly Tyr Arg His Ile Asp Cys Ala Tyr Val
        35                  40                  45
```

```
Tyr Gln Asn Glu His Glu Val Gly Glu Ala Ile Gln Glu Lys Ile Gln
    50                  55                  60

Glu Lys Ala Val Lys Arg Glu Asp Leu Phe Ile Val Ser Lys Leu Trp
65                  70                  75                  80

Pro Thr Phe Phe Glu Arg Pro Leu Val Arg Lys Ala Phe Glu Lys Thr
            85                  90                  95

Leu Lys Asp Leu Lys Leu Ser Tyr Leu Asp Val Tyr Leu Ile His Trp
            100                 105                 110

Pro Gln Gly Phe Lys Ser Gly Asp Asp Leu Phe Pro Lys Asp Asp Lys
            115                 120                 125

Gly Asn Ala Ile Gly Gly Lys Ala Thr Phe Leu Asp Ala Trp Glu Ala
    130                 135                 140

Met Glu Glu Leu Val Asp Glu Gly Leu Val Lys Ala Leu Gly Val Ser
145                 150                 155                 160

Asn Phe Ser His Phe Gln Ile Glu Lys Leu Leu Asn Lys Pro Gly Leu
                165                 170                 175

Lys Tyr Lys Pro Val Thr Asn Gln Val Glu Cys His Pro Tyr Leu Thr
            180                 185                 190

Gln Glu Lys Leu Ile Gln Tyr Cys His Ser Lys Gly Ile Thr Val Thr
            195                 200                 205

Ala Tyr Ser Pro Leu Gly Ser Pro Asp Arg Pro Trp Ala Lys Pro Glu
    210                 215                 220

Asp Pro Ser Leu Leu Glu Asp Pro Lys Ile Lys Glu Ile Ala Ala Lys
225                 230                 235                 240

His Ser Pro Ser Leu
            245
```